United States Patent
Bert et al.

(10) Patent No.: US 9,694,203 B2
(45) Date of Patent: Jul. 4, 2017

(54) METHOD FOR PREPARING AN IRRADIATION PLAN FOR A MOVING TARGET VOLUME WITHOUT A MOVEMENT COMPENSATION

(71) Applicants: Christoph Bert, Uttenreuth (DE); Christian Graeff, Weiterstadt (DE)

(72) Inventors: Christoph Bert, Uttenreuth (DE); Christian Graeff, Weiterstadt (DE)

(73) Assignee: GSI HELMHOLTZZENTRUM FUER SCHWERIONENFORSCHUNG GMBH, Darmstadt (DE)

( * ) Notice: Subject to any disclaimer, the term of this patent is extended or adjusted under 35 U.S.C. 154(b) by 386 days.

(21) Appl. No.: 14/365,109

(22) PCT Filed: Nov. 5, 2012

(86) PCT No.: PCT/EP2012/071853
§ 371 (c)(1),
(2) Date: Sep. 29, 2014

(87) PCT Pub. No.: WO2013/087297
PCT Pub. Date: Jun. 20, 2013

(65) Prior Publication Data
US 2015/0038762 A1    Feb. 5, 2015

(30) Foreign Application Priority Data
Dec. 13, 2011  (DE) .................. 10 2011 056 339

(51) Int. Cl.
*A61N 5/10*    (2006.01)

(52) U.S. Cl.
CPC .......... *A61N 5/103* (2013.01); *A61N 5/1031* (2013.01); *A61N 5/1037* (2013.01);
(Continued)

(58) Field of Classification Search
CPC .. A61N 5/1031; A61N 5/1043; A61N 5/1071; A61N 2005/1072; A61N 5/103; A61N 5/1037
See application file for complete search history.

(56) References Cited

U.S. PATENT DOCUMENTS

2006/0074292 A1    4/2006  Thomson et al.
2008/0021300 A1*   1/2008  Allison ................ A61N 5/1031
                                                         600/407
(Continued)

FOREIGN PATENT DOCUMENTS

CN    101076282 A    11/2007
CN    101663068 A    3/2010
(Continued)

*Primary Examiner* — Christine H Matthews
*Assistant Examiner* — Joshua D Lannu
(74) *Attorney, Agent, or Firm* — Leydig, Voit & Mayer, Ltd.

(57) ABSTRACT

A method for preparing a radiation treatment plan for irradiating a target volume region moving in regions in an object with a moving particle beam includes determining, using a mapping function dependent on a movement state (k) of the moving target volume region, a dose input in at least one target point volume (Vj). The dose input is brought about by applying the particle beam to an irradiation point (Bi).

16 Claims, 5 Drawing Sheets (52) U.S. Cl.
CPC ......... *A61N 5/1043* (2013.01); *A61N 5/1071* (2013.01); *A61N 2005/1072* (2013.01)

(56) References Cited

U.S. PATENT DOCUMENTS

| | | |
|---|---|---|
| 2008/0081991 A1 | 4/2008 | West et al. |
| 2010/0074408 A1 | 3/2010 | Biert et al. |
| 2010/0301235 A1* | 12/2010 | Bert ................ A61N 5/103 250/492.3 |

FOREIGN PATENT DOCUMENTS

| | | |
|---|---|---|
| DE | 102007014723 A1 | 11/2008 |
| DE | 102007045879 A1 | 4/2009 |
| JP | 2008080131 A | 4/2008 |
| WO | 2005120641 A1 | 12/2005 |
| WO | WO 2008005129 A3 | 10/2008 |
| WO | 2011005329 A2 | 1/2011 |

* cited by examiner

METHOD FOR PREPARING AN IRRADIATION PLAN FOR A MOVING TARGET VOLUME WITHOUT A MOVEMENT COMPENSATION

CROSS-REFERENCE TO RELATED APPLICATIONS

This application is a U.S. National Phase application under 35 U.S.C. §371 of International Application No. PCT/EP2012/071853 (WO 2013/087297 A1), filed on Nov. 5, 2012, and claims benefit to German Patent Application No. DE 10 2011 056 339.3, filed Dec. 13, 2011.

FIELD

The invention relates to radiation treatment plans for irradiating target volume regions, and particularly to radiation treatment plans for irradiating moving target volume regions using moving particle beams.

BACKGROUND

The use of radiation of various types and energies for charging, for machining workpieces to be machined, or for altering material properties of workpieces to be machined has become widespread in the art for a wide range of fields of application.

In this context, photon radiation (in other words in particular charging with light, charging with X-ray radiation, UV light, infra-red light and the like) is not the only possible type of radiation; in particular, particle radiation may also be considered. In this context, the particles may be substantially as desired ("particles" in this context meaning in particular particles which have a rest mass, even though it may be extremely small). Hadrons and leptons may be mentioned purely by way of example, in particular including neutrinos, electrons, positrons, pions, mesons, protons, neutrons, atomic nuclei (for example He nuclei), atoms or molecules and ions (in particular including heavy ions such as oxygen ions, helium ions, neon ions or carbon ions).

What all these types of radiation have in common is that the radiation deposits a particular energy in the item charged with radiation. However, in some cases the manner in which this energy is deposited varies greatly. Whilst for example in the case of photon radiation the energy loss is related approximately exponentially to the material penetrated over wide energy ranges, particle beams, in this case in particular hadron particles (especially protons, ions and heavy ions), have a pronounced Bragg peak. The particles thus initially lose comparatively little energy on the path thereof upon penetrating material. Shortly before the particles come to rest, the majority of the energy is released into the material charged with the radiation. As a result of this Bragg peak, not only two-dimensionally structured dose charges, but in particular also three-dimensionally structured dose charges can be realised (in other words different deposited radiation doses at different depths in the irradiated object).

Not only may the type of radiation used vary, but so also may the type of objects charged with radiation. To name just a few technical fields of application, possible examples relating to charging with protons in structuring processes include masks and material removal or material application in the manufacture of structured semiconductor components (such as memory elements, microprocessors and the like).

Photons may also be used for cutting and/or welding workpieces (in particular if the photon radiation is in the form of a high-energy laser beam).

One example application for electron beams is electron beam welding, by means of which for example two metal workpieces can be welded together. Naturally, separation and structuring processes are also conceivable.

In medicine and veterinary medicine, radiation is used for therapeutic purposes. For example, it is known to use X-ray radiation for producing X-ray images (including three-dimensional images from CT (computed tomography) methods). Electron beams have also been used in medicine for several decades, for example for treating cancerous tumours. Treatment for tumours using protons and ions (in particular heavy ions) has also now become well established in medicine. Because of the previously described Bragg peaks of protons/ions/heavy ions, it is possible to charge a three-dimensionally defined and structured region (in particular a tumour) in a patient with radiation in a targeted manner by controlling a particle beam accordingly (for example as part of a scanning process), whilst the surrounding tissue is largely unaffected. Precisions in the millimeter range are now possible. In this context, in some cases widened particle beams are used, which are structured spatially resolved in terms of the energy thereof (and thus the penetration depth thereof into the tissue), for example using paraffin plates of varying thicknesses. As a rule, however, scanning methods are now generally used in which, by means of suitable deflection magnets and suitable energy variation (leading to a variation in penetration depth), a conventionally thin (pencil-thin) particle beam successively "approaches" the different volume regions to be charged with a dose of the object to be irradiated.

So as to be able to treat three-dimensional volume regions in a body (in particular to treat cancer in a patient), it is usually necessary to prepare a radiation treatment plan. In this context, a particular radiation pattern is computer-simulated (in other words a sequence with different x-y deflections of the particle beam and suitable particle energies of the particle beam) and the respectively resulting dose input into the body charged with the radiation is calculated as a function of location. This is because, although the deposited dose in the irradiated object is concentrated on the region of the Bragg peak, a particular dose is nevertheless deposited in particular in regions lying close to the radiation point along the particle path. In the context of radiation treatment planning, an attempt is made to prepare a radiation treatment plan in which a particular minimum dose is reliably exceeded within a desired target volume region to be irradiated (in such a way that for example cancer cells are reliably destroyed), but surrounding tissue is spared as much as possible, in other words a particular maximum dose is not exceeded. The maximum dose to be set in this context may vary greatly depending on the irradiated object region. If for example in medical applications particularly vital and/or radiation-sensitive tissue regions are present, these have to be spared to the maximum extent. In this context, the term OARs (organs at risk) is generally used. In this context, a particularly suitable radiation treatment plan for the respective use can take place by actuating the particle beam differently and/or by introducing the particle beam from a plurality of different directions (possibly also a number of different directions including pivoting which is continuous at least at times).

Particular problems occur if (sub-regions of) the object to be irradiated move. In this context, movement may include not only translational movements, but also twisting movements and/or compression or extension movements. In particular in combination with scanning methods, the movements of the object and those of the particle beam may "interfere" with one another and lead to comparatively poor radiation results if suitable countermeasures are not taken.

Various solution approaches have been proposed in the art so as to be able to irradiate moving target areas.

For example, a first solution approach involves using corresponding tracking of the particle beam to compensate the movement of the target volume region in the object. However, problems with this method include the greatly increased equipment complexity and the problem that dose deposition effects in object regions outside the actively irradiated irradiation point cannot be predicted in the advance radiation treatment planning. As a result, particular comparatively complex monitoring and compensation methods are necessary. Even determining the actual movement of the target area in the context of the actual irradiation is often found to be problematic or virtually impossible. In particular in medicine, certain types of movement are not accessible or are difficult to access by "tracking" of this type.

Another proposal involves determining all of the possible movement states in advance in the radiation treatment planning (for example by CT methods) and selecting the area irradiated during irradiation to be suitable and sufficiently large so that the region to be irradiated is in any case charged with a particular minimum dose. In this context, some (inherently undesirable) damage of the surrounding tissue is deliberately accepted (or deliberately included in the planning in the context of safety margins). A problem during planning is that in particular in medical applications an (internal) movement of a target volume region in the patient not only leads to a change in the geometric position of the corresponding volume region, but also has an additional effect on the penetration lengths of the particle beam into the tissue, in particular by way of expansion and compressive movements and the accompanying density changes.

A method for taking into account effects of this type has been disclosed for example in German Offenlegungsschrift DE 10 2007 014 723 A1. In this context, a planning target volume is determined in that initially a target volume equivalent to the minimum target volume in the body is determined in an imaginary homogeneous body. The equivalent target volume is expanded by a safety margin to determine the planning target volume. A problem with the method proposed therein is that the conversion to an imaginary homogeneous body is heavily dependent on the direction of incidence of the particle beam. Preparing/optimising a radiation treatment plan in which there is a radiation input from two or more different directions is not possible with the method proposed therein. However, methods of this type using different radiation input directions are desirable so as to reduce the exposure of surrounding tissue (in particular OAR tissue) in so far as possible.

Even though some improvements to the method described therein using suitable transformation and back-transformation algorithms have already been considered, known methods still have problems. In particular if a movement of the target volume region is combined with different irradiation directions, in known methods this may lead locally to deviations from a target dose to be deposited (known as incorrect dosing). Above all, however, "gaps" (local underdosing) in the irradiated area are highly undesirable, since they may make it possible for cancer cells to survive, and thus drastically jeopardise the treatment success.

There is thus still a need for a method for preparing a radiation treatment plan which is improved over methods known in the art. There is likewise a need for devices for preparing a radiation treatment plan which are improved over devices known in the art.

SUMMARY

In an embodiment, the present invention provides a method for preparing a radiation treatment plan for irradiating a target volume region moving in regions in an object with a moving particle beam, the method including determining, using a mapping function dependent on a movement state (k) of the moving target volume region, a dose input in at least one target point volume (Vj), the dose input being brought about by applying the particle beam to an irradiation point (Bi).

BRIEF DESCRIPTION

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

In an embodiment, the invention provides a method for preparing a radiation treatment plan for irradiating a target volume region which moves at least in regions in an object using a preferably moving particle beam, in which, using a mapping function, the respective dose input brought about by applying the preferably moving particle beam to an irradiation point is determined in at least one target point volume, in that the mapping function is additionally dependent on a movement state of the moving target volume region. The radiation treatment plan is a set of different control parameters for the preferably moving particle beam. The particle beam may use in particular hadron and/or lepton particles, in particular protons, helium ions, neon ions and/or other ions, preferably heavy ions. The radiation treatment plan may (especially in the case of a moving particle beam) in particular be considered as a time-dependent function of a migrating irradiation point. Thus, an irradiation point may be taken in particular to mean an individual set of parameters for the particle beam (in particular a tuple of numbers). Parameters may in particular include the energy of the particles in the particle beam, the particle type, the ionisation, the deposition in the x-y direction (in other words deflection of the particle beam in the lateral direction), the diameter and/or the shape of the particle beam and the like. The preferably moving particle beam may for example be moved in the form of spot scanning (particle beam is switched off between two grid positions; the beam dwells on the individual grid positions for a particular time), a raster scanning method (the beam dwells on each grid point for a different time; however, there is no switching off of the beam between two grid positions) or a continuous scanning method (particle beam is moved continuously at a fluctuating speed). The dose input at an irradiation point is based in particular on the duration for which particles are introduced to the point in question and/or the particle luminescence at this moment. However, in principle it is also possible to use a stationary particle beam, which is accordingly widened and/or produces a space-resolved and energy-resolved wide particle beam by way of suitable measures (for example using a paraffin plate of varying thickness). Whilst the irradiation point is thus preferably present in parameters which control the accelerator, the target point volume is generally a geometrically present volume (in particular in Cartesian coordinates). The conversion from irradiation points to a target point volume is complex and in particular non-linear. This is because in the "geometric space", which can be determined for example using imaging methods (for example CT or NMR; CT=computed tomography; NMR=nuclear magnetic resonance), the effective range of a particle beam in a material (and thus also, among other things, the position of the Bragg peak in a "targeted" irradiation point) generally depends on additional factors, in particular on the density and/or material composition of the irradiated material. For example, when irradiating a pulmonary lobe, an air-filled cavity may be irradiated (extremely low density), and on the way a rib may also be irradiated (high density). All materials lying on the path of the particle beam have a major influence on the effective position of the Bragg peak, and thus on the distribution of the effectively deposited dose in the different target point volumes, and thus in geometric space. The type and density distribution of the tissue may vary greatly during a movement of the moving target volume region. For example, as a result of a patient breathing, part of a rib may migrate out of the particle path of the particle beam, and at the same time the air-filled volume in the lung (and thus the distance covered through air) may become much longer or shorter. Accordingly large effects occur in terms of the position of the Bragg peak and/or of the dose input in the target point volumes. A relatively large set of target point volumes can be used to prepare the radiation treatment plan, in particular a variety of target point volumes which comprises a larger region of an object to be irradiated (in particular regions to be irradiated and/or regions not to be irradiated). The regions to be irradiated may in particular be the ITV ("internal target volume"). The ITV generally constitutes the areas which a volume region to be irradiated (generally referred to as the CTV or "clinical target volume") can take on when all (realistically expectable) movement states are taken into account. It is thus generally a type of "geometric envelope volume". Preferably, the size is selected in such a way that the volume which can be reached by the particle beam (plus a safety margin) is resolved into finite target point volume elements (known as voxels). In particular the region of the object which can be reached means the region which can be reached by using deflection measures of the particle beam and/or by varying the energy of the particle beam (or which it should be possible to reach during a provided radiation scheme). The mapping function may be present or be provided in substantially any desired manner. In particular, it is possible to provide an analytical formula or analytical approximation formula. It is also conceivable to use tables of values (in which the desired values are "looked up"), interpolation methods and mixtures of said methods. In particular, direct mapping without detours can be achieved using the mapping function, for example without an initial conversion to a homogeneous equivalent phantom body which is subsequently used for further calculations. However, this does not exclude the possibility that the mapping function is present in a "plurality of parts", for example using a transformation function (for example a transformation matrix) and a HU-LUT (Hounsfield unit look-up table), which is often used in particle therapy and by way of which the geometric volume regions are converted into radiographic volume regions (in which different material thicknesses are taken into account; often a conversion into "water-equivalent body"; in this context the term "water-equivalent path length" (WEPL) is often also used). The combination function consisting of a transformation function of this type and a HU-LUT can subsequently form the mapping function within the meaning of the present application. It is also possible to determine a respective individual ITV for each individual one of the different movement states. An additional transformation function (which need not necessarily correspond with the one disclosed above) may be used for joint optimisation of all ITVs produced in this manner, and converts the water-equivalent ranges of the target volume in question, which are dependent on the irradiation direction, into a target volume which is equally valid for all irradiation fields and independent of the irradiation direction.

The method can be carried out in such a way that the mapping function takes into account at least the change in range of the preferably moving particle beam, in particular the change in range of the preferably moving particle beam which is brought about by changes in density, in particular radiographic changes in density, in the particle beam direction. Radiographic changes in density may be taken in particular to mean a change of density in water-equivalent units (WEPL—"water-equivalent path length"). In particular by way of this development of the proposed method, it is possible for a very wide range of types of irradiation fields to be taken into account and optimised simultaneously in the radiation treatment planning, without excessively increasing the risk of underdosed volume regions. In particular, it is possible to prepare a radiation treatment plan even if there are both different particle irradiation directions and moving target volume regions.

It is particularly preferred for the mapping function additionally to be dependent on an irradiation direction of the preferably moving particle beam. As mentioned previously, in certain objects (in particular in the medical field with greatly varying material region densities), in some cases the radiographic density, and thus the ultimate position of the Bragg peak of the particle beam, depend heavily on the path taken by the particle beam through the object to be irradiated. Accordingly, in particular in the medical field, the position of the Bragg peak generally depends heavily on the irradiation direction of the particle beam. If this dependency is taken into account (at least in part) by the mapping function, the quality of the resulting radiation treatment plan can in some cases be greatly improved.

In the proposed method, the radiological effectiveness on the material to be charged with the radiation can be taken into account. In particular in medicine, the RBE (relative biological effectiveness) may additionally be taken into account in this context, for example.

In the proposed method, it is further proposed for the dose input into at least one target point volume to be determined at least at times and/or at least in part for different movement states and/or for different irradiation directions in a mutually distinguishable manner. In other words, for each movement state and/or for each different irradiation direction (if both are taken into account, it is possible in particular to use a correspondingly large matrix which takes both effects into account), the respectively resulting dose distribution in the geometric space for this state or for this irradiation direction can be determined There is thus preferably (initially) no averaging of different movement states and/or different irradiation directions or similar. This development too makes it possible to achieve a generally particularly good radiation treatment plan.

In the method, at least some of the target point volumes can be classified as target point volumes to be irradiated and/or as target point volumes not to be irradiated. In particular, for target point volumes to be irradiated a minimum radiation dose which is to be exceeded and/or for target point volumes not to be irradiated a maximum radiation dose which must not be exceeded may be defined. Naturally, it is possible for different limit values to be defined in different regions both for target point volumes to be irradiated and for those not to be irradiated. In this way it is possible for example to take particularly sensitive tissue into account especially in the calculation and/or to ensure to a particular degree in the calculation that tissue (material) to be destroyed actually is destroyed.

Preferably, the method is carried out to the effect that to calculate the radiation treatment plan for a plurality, preferably all, of the target point volumes in different movement states a substantially identical irradiation pattern is used. In other words, for each movement state the respectively resulting dose distribution is determined, and the respectively resulting dose distributions can be optimised in distribution using suitable mathematical methods. This proposal is based on the consideration that in a non-movement-compensated irradiation method the target volume region to be irradiated may be in any movement phase. This is to be taken into account accordingly in the calculation.

In the method, it is further proposed for a plurality of movement states, in particular a plurality of movement states which describe a typical movement sequence, to be used in preparing the radiation treatment planning. In this context, a good compromise should preferably be found between, on the one hand, particularly fine resolution (and thus better results) and, on the other hand, a manageable computation time. What is often also decisive in practice is how many movement states are available or can be made available (for example by medical personnel who have produced a CT scan). The movement states and/or the typical movement sequence may in particular be obtained prior to the actual irradiation by imaging processes. In particular, CT methods and/or NMR methods, in particular working in a time-resolved manner, are suitable in this context.

However, it is also possible to use a subset of movement states for preparing the radiation treatment plan. In some cases, this can make it possible to reduce the computation time considerably, even though the quality of the radiation treatment plan is not substantially impaired. For example, a particularly suitable subset of movement states are movement states which are taken on particularly frequently and/or for particularly long periods and/or movement states which represent extreme positions (for example a fully inhaled and fully exhaled state in a breathing cycle).

A target dose and/or a tolerable dose can be assigned to at least parts of the target point volume. Values of this type may be used as particularly suitable input parameters for an automated optimisation of the radiation treatment plan. In this context, a tolerable dose may also take the form of a lower limit value and/or an upper limit value.

In the method, it has been found that handling is particularly simple in practice if a data matrix is used as the mapping function at least at times and/or at least in regions. In this way, computation time can generally be saved (in particular in relation to a function in analytical form). In modern computers, it is specifically calculation time that is a problem, not storage. In this context, it should be noted that even for complex systems having tens of thousands of target point volumes only storage in the gigabyte range is required, and this can be provided in a comparatively simple and cost-effective manner with the computers that are currently commercially available.

In the method, the target dose distribution can be optimised. In particular, the optimisation may be automated, specifically using optimisation methods known per se in multi-dimensional systems. In particular, it is possible to optimise an individual joint ITV directly using the mapping function. In addition or alternatively, however, it is also possible to determine a respective, preferably optimised ITV for each individual movement phase, which covers the target volume in this movement state. For jointly optimising all ITVs selected in this manner, a transformation rule may be used which converts the respective ITV into a joint target volume which is independent of the irradiation direction. Said volume can subsequently (again) be optimised.

In a further development of the method at least two movement states and/or at least two directions of the radiation input are taken into account when calculating the radiation treatment plan. However, it is advantageous for a larger number of movement states and/or directions of the radiation input to be taken into account, since this generally increases the quality of the radiation treatment plan.

In another embodiment, the present invention provides a device for preparing a radiation treatment plan for treating a moving target volume region using a preferably moving particle beam, the device being configured and set up so as to carry out a method having the above-disclosed properties. A device of this type can thus comprise the above-disclosed advantages and properties in an at least analogous manner. Further, the device can be developed within the meaning of the preceding description, at least analogously.

The device can be configured in such a way that it comprises at least one program-controlled computation unit. In particular computers are conceivable (for example personal computers and/or workstations and/or large computers). Devices of this type are found to be particularly suitable for carrying out the method because they are simple to program and readily available commercially.

Figure 1A:
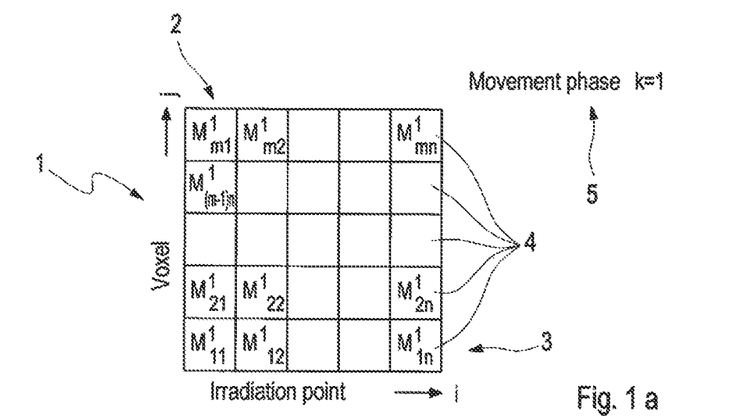
FIG. 1 is a possible example of a mapping function between the irradiation point and the target point volume for a plurality of movement phases.
Figure 1B:
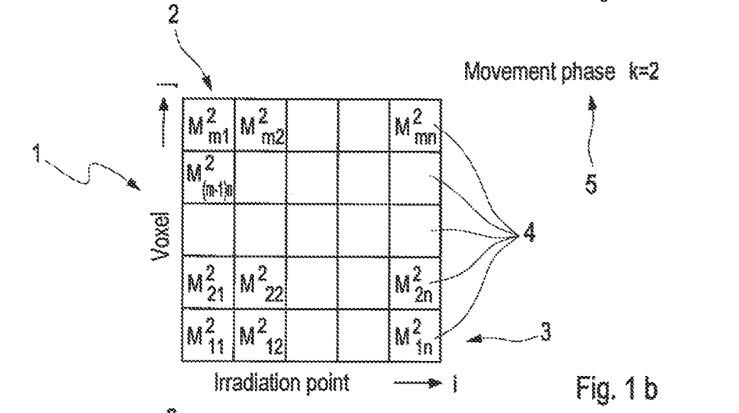
Figure 1C:
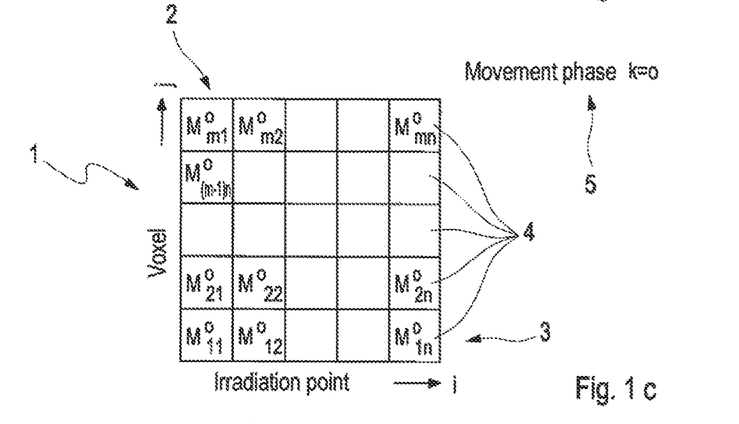

FIG. 1 is an example of a possible mapping function by means of which the effective dose input into different volume regions $V_j$ brought about by charging an irradiation point $B_i$ can be implemented, in accordance with a possible embodiment. In this case, the mapping function is in the form of a (multi-dimensional) matrix 1. In this context, the dimension of the matrix 1 is determined from the number of movement phases to be taken into account (in FIG. 1 these different movement phase "planes" are shown one beneath the other).

For preparing the mapping matrix 1, a body to be irradiated is subdivided into a relatively large number of individual finite volume elements, known as voxels $V_j$. The volume region of the target object to be subdivided into voxels $V_j$ of this type is selected to be larger than the target volume actually to be charged with radiation (for example a tumour to be treated or a corresponding target volume region of a radiation phantom), including the enlargement of the area to be irradiated brought about by an (internal) movement of the actual target volume region and/or taking into account a safety margin. This is because, when preparing the radiation treatment plan, it has been found to be expedient for the usual movements of the target object also to be taken into account when preparing the radiation treatment plan. In this way, the radiation treatment plan can be optimised both in relation to a sufficient dose input into volume regions to be charged with a dose and in relation to a minimum possible dose input into volume regions which are not to be charged with a dose per se (although this generally cannot be completely prevented). It is especially relevant in particular to avoid a dose input into particular volume regions involving tissue which is particularly sensitive and/or requires particular protection for other reasons (often referred to as OARs—organs at risk). Conversely, it is also not necessarily required for the entire object to be irradiated to be taken into account in the subdivision into individual voxels $V_j$. If the target area to be irradiated is relatively small by comparison with the entire object, the extent of the improvement in the radiation treatment plan is generally not comparable with the increased computational cost if far-removed areas are also taken into account when preparing the radiation treatment plan. An example of this is treating a tumour positioned in the lung and taking into account a patient's legs (this generally not being expedient).

Depending on the size of the selected volume and the subdivision thereof into individual voxels $V_j$ (precision), there will be a corresponding number n of voxels $V_j$. This number n of individual voxels $V_j$ has an effect on the size of the resulting mapping matrix 1.

Further, a set of irradiation points $B_i$ which are approached by the particle beam during the irradiation is predetermined. In this context, it is likewise not absolutely necessary for all of the regions which are physically reachable using the respective system (in particular variations in x and y deflection and in energy, corresponding to the z deflection) to be taken into account. Instead, usually sets of parameters are used which are in an expedient relationship to the volume to be treated. In this context, the irradiation points $B_i$ correspond to some extent to the parameters of the particle beam, and thus in particular deflection of the beam and energy of the particles in the particle beam. In this context, the number m of irradiation points $B_i$ also has an effect on the size of the mapping matrix 1. If an individual irradiation point $B_i$ is now "approached" by a particle beam, not only does this bring about a radiation input into an individual voxel $V_j$ (or into a very small number of directly mutually adjacent voxels $V_j$), but there will also be a radiation input into remotely positioned voxels $V_j$. In particular, there will be a radiation input into voxels $V_j$ positioned in regions through which the particle beam passes on the way to its target (proximally positioned regions). Moreover, the type of tissue irradiated has an effect on the effective length of the particle beam in the object. For example, if this is a dense tissue (in particular water-rich tissue), this reduces the path length covered by the particle beam until it "comes to rest". By contrast, if there are low-density regions (for example air-filled cavities, for example a lung in the inhaled state), the particle beam covers a much larger distance in the object for the same energy. This relationship is explained in greater detail in the following with reference to FIG. 3.

Both effects, in other words both the penetration depth of the particle beam (and thus the relationship between the geometric volume—which can be determined for example using imaging methods—and the radiological location taking into account different material density) and also the dose input into remotely positioned volume regions (voxels $V_j$), are described by the value of the respective matrix elements $M_{ij}^k$. An individual coefficient $M_{ij}^k$ thus describes the dose input into the $j^{th}$ voxel when the $i^{th}$ irradiation point is approached. The individual coefficients are thus standardised in terms of the number of particles. When preparing a radiation treatment plan, the provided radiation treatment plan is therefore "tested" computationally, and the effective distribution in the geometric volume (in the voxels $V_j$), obtained using the mapping matrix 1, is determined. Depending on the particle fluence (in other words number of applied particles per radiation point), the individual coefficients $M_{ij}^k$ have to be multiplied in accordance with the particle fluence.

However, the distribution of the coefficients varies in the presence of an (internal) movement in the target region of the object to be irradiated. This is because an internal movement results not only in a geometric displacement of the corresponding target area, but also to changes in density in the surrounding material (tissue). This has corresponding effects on the penetration depth of the particle beam.

Therefore, to take these effects into account, not only an individual mapping matrix 1 for a particular movement phase k (in FIG. 1a a movement phase k=1) is used, but rather a plurality of individual mapping matrices 1, which each describe different movement phases k. The movement phases k (and the respective target volume region change) may for example be obtained in advance using imaging methods, such as CT methods and/or NMR methods. In this context, the number of movement phases k=1 . . . o should be chosen in an expedient manner. In particular, the change in location brought about by the movement between two individual movement phases k should be in an expedient ratio (typically in the range of 1) to the resolution (size) of the individual voxels $V_j$.

This results in a plurality of mapping matrices 1 for the respective different movement phases k=1 . . . o.

Merely for completeness, it should be noted that it is of course also possible to make an individual mapping matrix correspondingly larger (in other words generally o times as large), in such a way that it can take on the required coefficients (in spite of being of the same dimension).

Merely for completeness, it should be noted that the number of movement phases k can be reduced if the method is used in combination with gating methods. In gating methods, a dose is only applied if the target volume is located in particular movement phases k. Naturally, only these movement phases subsequently have to be taken into account for the radiation treatment planning.

The irradiation direction of the particle beam into the target volume may have an effect on the distribution of the coefficients of the mapping matrix 1. Accordingly, the mapping matrix 1 is to be expanded suitably if appropriate.

In this context, when calculating a radiation path during radiation treatment planning, an individual voxel vector $\underline{V}^k$ is not used to describe the target allocation in each voxel element $V_j$, j=1 . . . n, as was often done previously in the art. Instead, an individual voxel vector $\underline{V}^k$ is used for each movement phase. However, the target allocation is not changed in this context, and so the requirements of the dose allocation are transferred from one movement phase to all movement phases. The length of the vector of the particle allocations (irradiation points $B_i$) is not changed in this context. By way of the mapping matrices having the entries $M_{ij}^k$, the voxel vectors $\underline{V}^k$ are linked to the vector $\underline{B}$ of the particle allocations. This procedure is based on the consideration that during irradiation without tracking (and optionally also without gating) it should be assumed that the actual target volume may be in any movement phase during the irradiation. (If gating methods are used, there is accordingly a limitation to particular movement phases).

In the subsequent optimisation of the radiation treatment plan, an attempt is subsequently made to select (optimise) the particle allocations in such a way that they are optimised in terms of the target allocations (target dose) from the individual voxel vector specifications $\underline{V}^k$.

In this context, the target allocation may in particular be a particular target dose per voxel (including a tolerable fluctuation). In particular, it is also possible for the target dose and/or the tolerable fluctuation width to be provided with a particular minimum value below and/or with a particular maximum value above (in particular for OARs).

The major advantage of the disclosed method is that in particular multi-field optimisation is possible without this having to lead to undesirable overdoses or underdoses. This is explained in greater detail with reference to FIG. 2. The respective FIG. 2a-2c each show single-field irradiation on the left and dual-field irradiation with a radiation dose 21, 22 from different directions on the right.

Figure 2A:
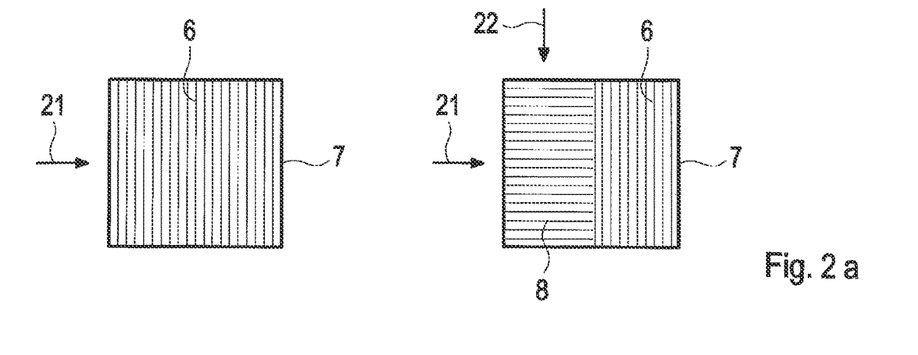
FIG. 2 shows effects on the total dose input when using different irradiation directions and applying different radiation treatment plan optimisation methods.

In FIG. 2a, a dose distribution 6 (vertical lines) is indicated by a radiation input 21 from the left (indicated by an arrow) through vertical lines. In this context, the target area 7 is located in a reference phase for which the radiation treatment plan is optimised. In this reference phase, it is also possible for a dose input to take place from two different directions 21, 22 (indicated by arrows). In this context, the radiation treatment plan is selected in such a way that the first dose input 6 (vertical lines) brought about by the particle beam 21 on the left in the drawing and the second dose input 8 (horizontal lines) brought about by the particle beam 22 from above combine to form a seamless dose input.

Figure 2B:
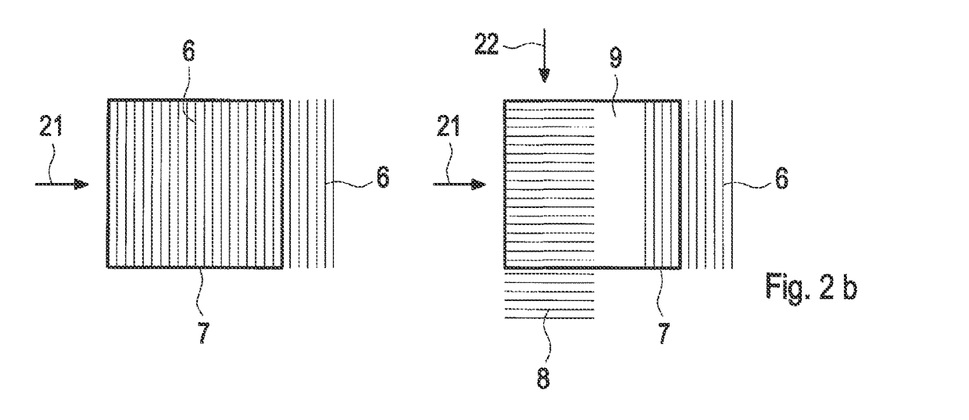

If there is now a reduction in density in the target area 7, the range of a particle beam 21, 22 increases. Accordingly, the area of the first dose input 6 becomes "longer" in a manner corresponding to the reduction in density. The "left edge" of the first dose input area 6 remains unchanged, since it is assumed that there is no change in density outside the target area 7. In the single-field case (left in the drawing), there is thus an undesirable dose charge into material which is not to be charged per se, located to the right of the target area 7. This effect is already undesirable. However, the generally greater drawback of possible underdosing in the material to be irradiated (which for example may jeopardise the treatment success in cancer treatment in that cancer cells are not destroyed) does not occur.

However, if two different particle irradiation directions are used, not only the corresponding dose input fields 6, 8 become longer. Since the "left edge" of the first dose input filed 6 is now in the centre of the target area 7 (and thus in a region where density variation has occurred), the "left edge" of the dose input field 6 is displaced accordingly. This results in an underdosed region 9 which, as mentioned previously, greatly jeopardises the treatment success in the case of cancer treatment.

Figure 2C:
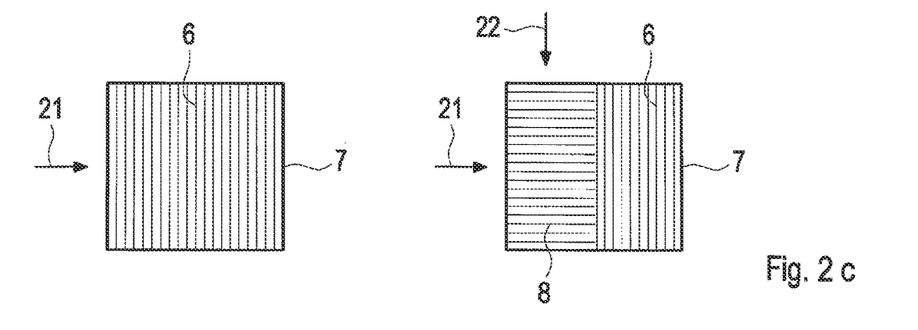

However, if an individual optimisation is carried out for the movement state shown in FIG. 2b, by the method described above, homogeneous irradiation inputs can be achieved again, in particular without underdosing. This is indicated in FIG. 2c. There may potentially also be a (somewhat) stronger dose in the boundary region between the first dose input field 6 and the second dose input field 8.

FIG. 3 again shows the change in the range of a particle beam due to changes in density.

Figure 3:
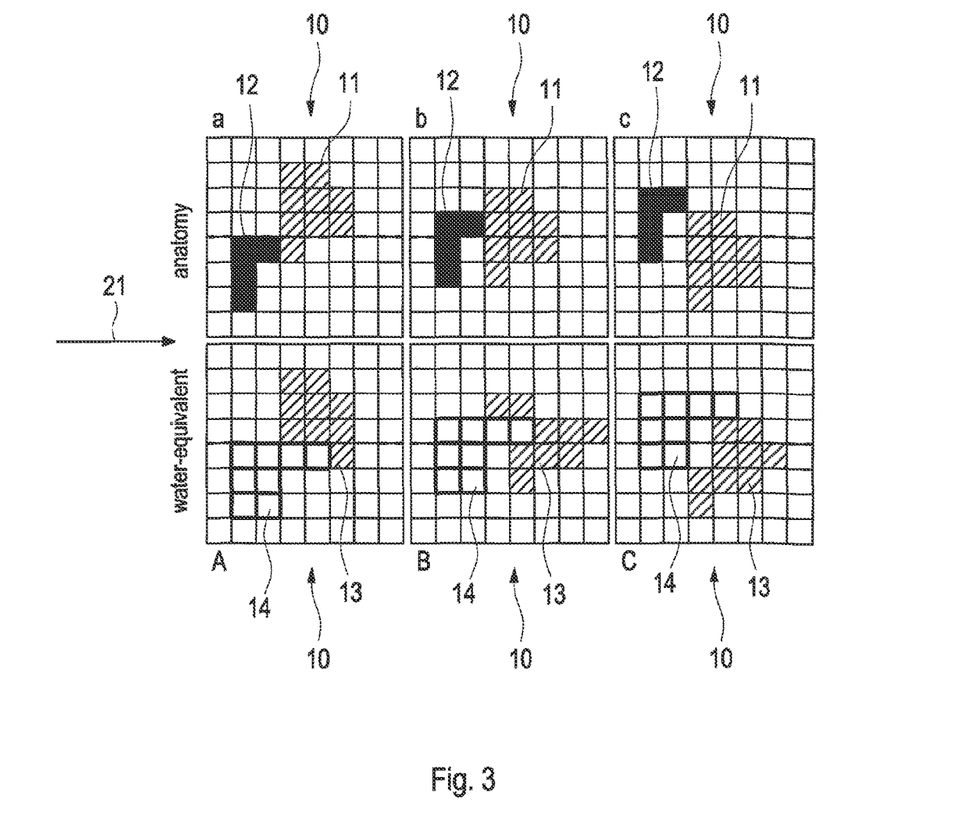
FIG. 3 shows the effect of different tissue densities in the presence of movements on the site of the deposited dose.

In the first line, a target area 10 to be irradiated is shown in three different movement phases a, b, c. In the target area 10, a moving target volume 11 to be charged with a dose is illustrated. Further, a likewise moving low-density region 12 is present, proximally upstream from the target volume 11.

Since the (radiologically) low-density region 12 changes the range of the particle beam, this results in a different target volume 13 to be irradiated "from the point of view of the particle beam". In FIG. 3, for simplicity, it is assumed that a volume element in the higher-density region 12 has twice the radiological density of the other tissue towards the particle beam. Accordingly, one volume element in the high-density region 12 in geometric space corresponds to two volume elements 14 in the "radiological coordinate image".

As can be seen, the target volume 13 in the radiological image varies considerably between the different movement phases A, B, C (lower line in FIG. 3).

Figure 4:
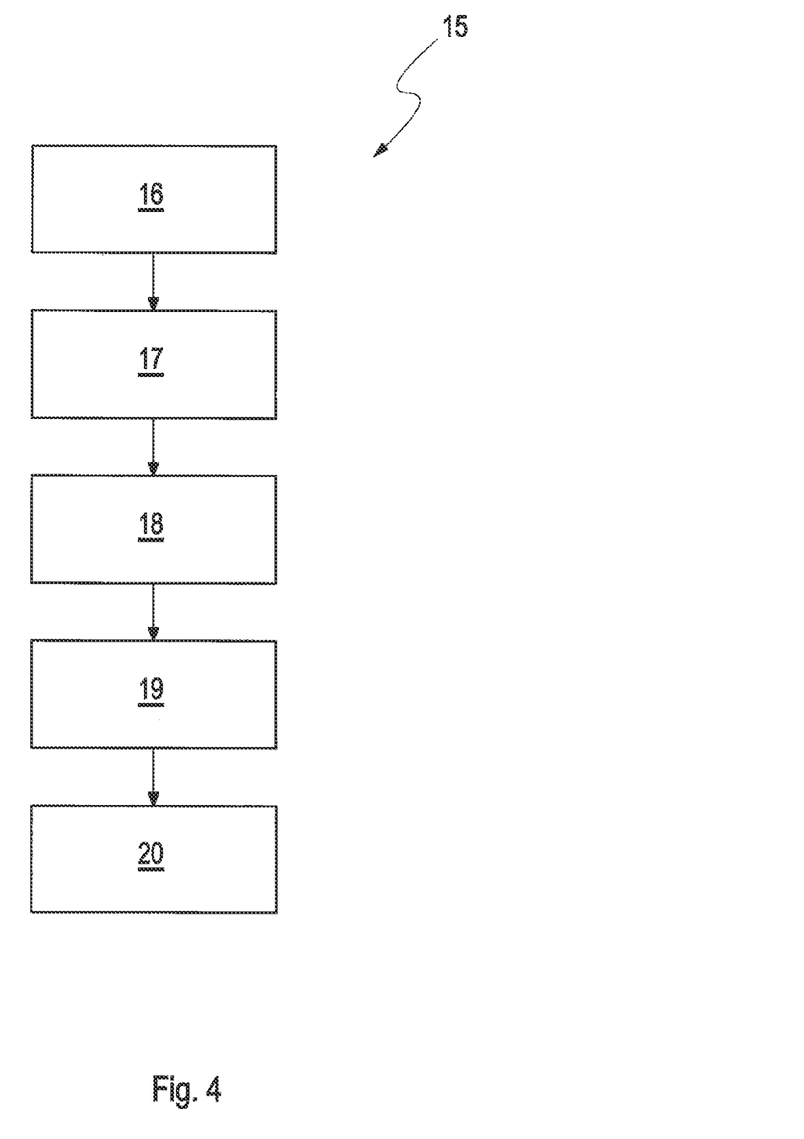
FIG. 4 is a schematic flow chart of a method for preparing a radiation treatment plan.

FIG. 4 outlines the proposed method briefly in the form of a flow chart 15. Initially, in a first step 16, the geometric position of the target region 11 to be irradiated (and optionally also the geometric position of areas not to be irradiated, such as OARs) is determined in the different movement phases. By way of example, CT and NMR methods are suitable for this purpose in the medical field.

Once this information has been obtained, the volume to be irradiated during irradiation is determined in the different movement phases (step 17). In the medical field, this is referred to as the CTV (clinical target volume). This is generally enlarged by safety margins, in such a way that the minimum doses to be achieved in the region to be irradiated are reliably reached (even if this may potentially result in some damage to healthy tissue).

Subsequently, in step 18 the mapping matrix is prepared (for example mapping matrix 1 as in FIG. 1).

Using this mapping matrix, individual "test radiation treatment plans" are now calculated and optimised using optimisation algorithms (step 19). In this way, an optimised radiation treatment plan is ultimately obtained and is outputted in step 20.

Figure 5:
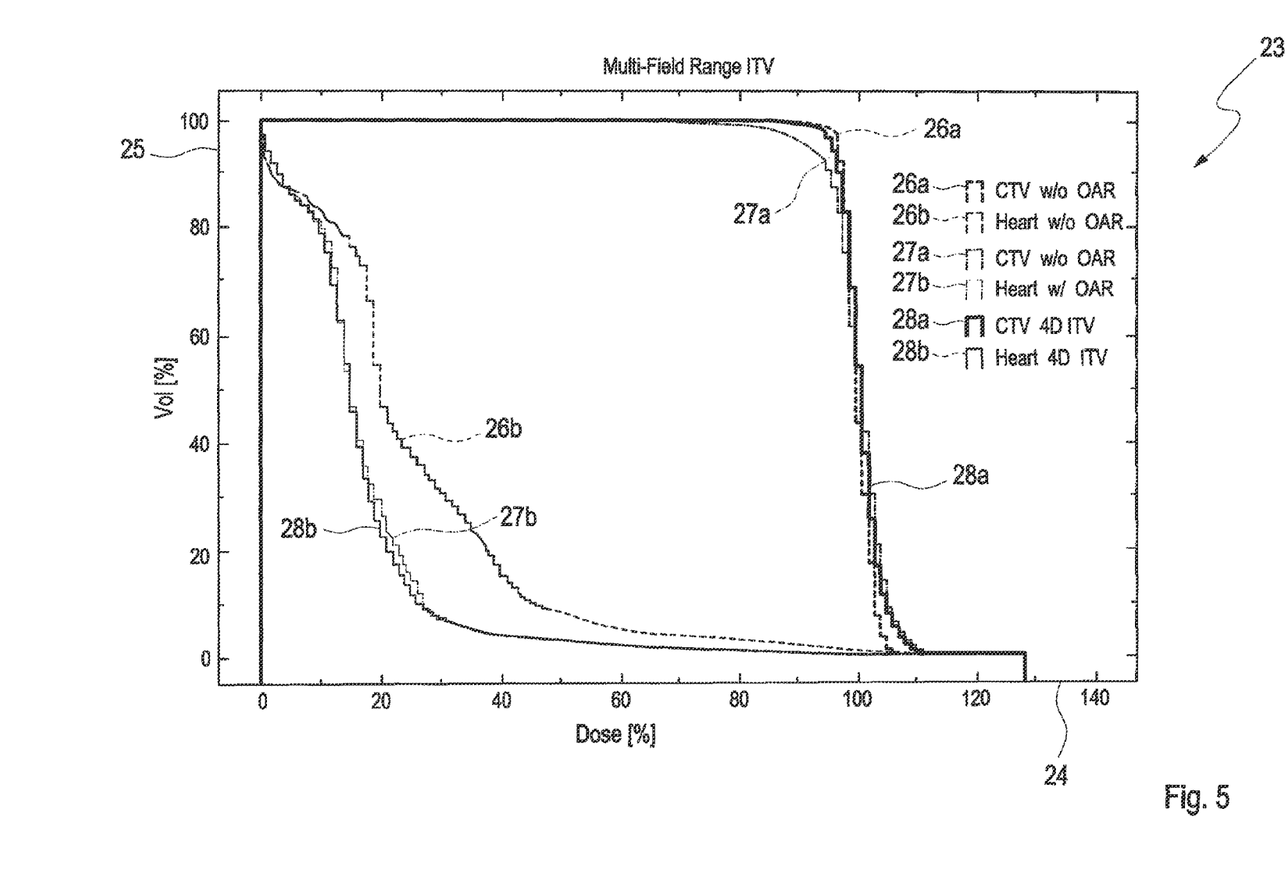
FIG. 5 is a dose-volume histogram (DVH) of different types of irradiation method on a prototype.

FIG. 5 shows a DVH (dose-volume histogram) 23 illustrating the dose input into a prototype for different irradiation methods. This simulates a tumour located on the lung. A DVH 23 shows the dose input in percent on the x-axis 24, whilst the proportion of the tissue to be charged with the corresponding dose is shown on the y-axis 25. An ideal dose input for the tissue regions to be irradiated would be a rectangular line along the line for 100 percent by volume and 100 percent dose. Accordingly, an ideal radiation input for tissue regions not to be irradiated would be a rectangular line along the line for 0 percent by volume and 0 percent dose. Three irradiation methods (26, 27, 28) are shown, and in each case tissue regions to be irradiated (26a, 27a, 28a) are shown at the top right in FIG. 5 and tissue regions not to be irradiated (26b, 27b, 28b) are shown at the bottom left in FIG. 5.

Line 26 represents an irradiation result which was achieved using a multi-field ITV radiation treatment plan (ITV=internal target volume). As can be seen from the line 26a for tissue regions to be irradiated, there is a good dose allocation for tissue regions to be irradiated. However, this is at the price of a high dose input into tissue regions not to be irradiated (line 26*b*). In the case of sensitive organs (in particular OARs, organs at risk), this is not acceptable.

There is an improvement if a multi-field ITV radiation treatment plan is used which takes OARs (in this case the heart) into account. The result can be seen from lines 27. It can clearly be seen that the dose input into tissue regions not to be irradiated (line 27*b*) is greatly reduced. At the same time, however, it can also be seen that in some cases there is a poor dose allocation into tissue regions which actually are to be irradiated (underdosing), and this is likewise problematic (line 27*a*).

Much better results are achieved both for tissue regions to be irradiated and for tissue regions not to be irradiated just by using a multi-field ITV radiation treatment plan in which (only!) two movement phases are taken into account (in this case fully inhaled and fully exhaled). This can be seen from the continuous black line 28. The dose allocation into tissue regions to be irradiated (line 28*a*) is very good, and so is the (low) dose allocation into tissue regions not to be irradiated (line 28*b*).

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 1. mapping matrix
2. voxel vector
3. irradiation point vector
4. matrix coefficient
5. movement phase
6. first dose field
7. target area
8. second dose field
9. underdosed region
10. target area
11. target volume
12. (geometrically) high-density region
13. (radiological) target volume
14. (radiological) high density
15. flow chart
16. determining ITV
17. determining CTV
18. preparing mapping matrix
19. optimising radiation treatment plan
20. outputting radiation treatment plan
21. radiation input from left
22. radiation input from above
23. DVH (dose-volume histogram)
24. x-axis
25. y-axis
26. multi-field ITV without OARs
27. multi-field ITV with OARs
28. multi-field ITV with OARs and two movement phases

The invention claimed is:

1. A method for generating, by a program-controlled computer, a set of control parameters for controlling a radiation generating device so as to irradiate an at least partially moving target region with a moving particle beam, wherein irradiation points ($B_i$) to be irradiated by the particle beam are present in the set of control parameters, the method comprising:

defining a plurality of movement phases of the moving target region;

determining, for each of the plurality of movement phases, a geometric position of the moving target region;

defining a plurality of target point volumes ($V_j$) within the moving target region;

providing, for each of the plurality of target point volumes ($V_j$), a value in connection with a target dose to be deposited in the target point volume ($V_j$);

generating a mapping function between the irradiation points ($B_i$) to be irradiated by the particle beam and the target point volumes ($V_j$), wherein the mapping function includes data indicating, for each of the plurality of movement phases, a dose input into at least one of the target point volumes ($V_j$) when an ith irradiation point ($B_i$) is approached; and generating, using the mapping function, the set of control parameters for controlling the radiation device so as to irradiate the at least partially moving target region with the moving particle beam.

2. The method of claim 1, wherein the mapping function takes into account a change in range of the moving particle beam brought about by changes in density of material in a path of the moving particle beam.

3. The method of claim 1, wherein the mapping function is dependent on an irradiation direction of the moving particle beam.

4. The method of claim 1, wherein the generating a mapping function involves determining, in a mutually distinguishable manner for each of the plurality of movement phases, a dose input into at least one of the target volumes ($V_j$) when an ith irradiation point ($B_i$) is approached for at least one of different movement phases and different irradiation directions.

5. The method of claim 1, wherein the mapping function includes data indicating, for each of the plurality of movement phases, a dose input in multiple of the target point volumes (Vj), wherein each of the multiple target point volumes (Vj) is classified as one of a target point volume to be irradiated and a target point volume not to be irradiated.

6. The method of claim 1, wherein the mapping function includes data indicating a dose input in a multiple of the target point volumes ($V_j$) for different movement phases for a substantially identical irradiation pattern.

7. The method of claim 1, wherein the plurality of movement phases of the moving target region describe an entirety of a typical movement sequence of the moving target region.

8. The method of claim 1, wherein the plurality of movement phases of the moving target region exclude a portion of an entirety of a typical movement sequence of the moving target region.

9. The method of claim 1, wherein at least one of a target dose and a tolerable dose is assigned to at least parts of the moving target region.

10. The method of claim 1, wherein the mapping function is a data matrix.

11. The method of claim 1, wherein the dose input into at least one of the target point volumes ($V_j$) when an ith irradiation point ($B_i$) is approached is optimized according to the dose values provided.

12. The method of claim 1, wherein the generating, using dose distributions for each of the plurality of movement phases, the set of control parameters for controlling the radiation device so as to irradiate the at least partially moving target region with the moving particle beam takes into account at least two directions of radiation input.

13. The method according to claim 1, wherein the value in connection with the target dose is one of a target dose value, a tolerable fluctuation width, a maximum dose value to be deposited in the target point volume, or a minimal dose value to be deposited in the target point volume.

14. A device for generating a set of control parameters for controlling a radiation generating device so as to irradiate an at least partially moving target region with a moving particle beam, the device comprising:

a program controlled computer configured to:
define a plurality of movement phases of the moving target region,
determine, for each of the plurality of movement phases, a geometric position of the moving target region,
define a plurality of target volumes ($V_j$) within the moving target region,
provide, for each of the plurality of target point volumes ($V_j$), a value in connection with a target dose to be deposited in the target point volume ($V_j$);
generate a mapping function between the irradiation points ($B_i$) to be irradiated by the particle beam and the target point volumes ($V_j$), wherein the mapping function includes data indicating, for each of the plurality of movement phases, a dose input into at least one of the target point volumes ($V_j$) when an ith irradiation point ($B_i$) is approached; and
generate, using the mapping function, the set of control parameters for controlling the radiation device so as to irradiate the at least partially moving target region with the moving particle beam.

15. The device according to claim 14, wherein the value in connection with the target dose is one of a target dose value, a tolerable fluctuation width, a maximum dose value to be deposited in the target point volume, or a minimal dose value to be deposited in the target point volume.

16. The device according to claim 14, wherein the dose input into at least one of the target point volumes ($V_j$) when an ith irradiation point ($B_i$) is approached is optimized according to the dose values provided.

* * * * *